United States Patent [19]
Schmidt

[11] Patent Number: 5,354,551
[45] Date of Patent: * Oct. 11, 1994

[54] ORAL AND DENTAL HYGIENE PREPARATION

[75] Inventor: Wolfgang Schmidt, Hamburg, Fed. Rep. of Germany

[73] Assignee: Desitin Arzneimittel GmbH, Hamburg, Fed. Rep. of Germany

[ * ] Notice: The portion of the term of this patent subsequent to Jul. 18, 2006 has been disclaimed.

[21] Appl. No.: 47,067

[22] Filed: Apr. 16, 1993

Related U.S. Application Data

[63] Continuation of Ser. No. 689,862, Aug. 13, 1991, abandoned.

[30] Foreign Application Priority Data

Oct. 14, 1989 [DE] Fed. Rep. of Germany ....... 3934416

[51] Int. Cl.$^5$ ...................... A01N 1/02; A45D 44/18; C11D 17/00
[52] U.S. Cl. ..................... 424/49; 424/401; 424/414; 252/91; 252/92; 15/104.94; 15/167.1; 15/210.1
[58] Field of Search ....................... 15/104.94, 176, 209, 15/210; 252/91, 92; 924/401, 49, 414

[56] References Cited

U.S. PATENT DOCUMENTS

| | | | |
|---|---|---|---|
| 1,411,681 | 4/1922 | Burlen | 15/104.94 |
| 1,421,911 | 7/1922 | Cohen | 15/104.94 |
| 1,637,153 | 7/1927 | Lawton | 15/167.1 |
| 1,960,192 | 5/1934 | Howard | 15/104.93 |
| 2,389,736 | 11/1945 | Muise | 15/104.93 |
| 2,665,528 | 1/1954 | Sternfield et al. | 15/104.94 |
| 2,673,364 | 3/1954 | Diveley | 15/104.93 |
| 2,893,036 | 7/1959 | Filler et al. | 15/167.1 |
| 3,902,509 | 9/1975 | Tundermann et al. | 15/104.94 |
| 4,515,703 | 5/1985 | Haq | 15/104.94 |
| 4,849,246 | 7/1989 | Schmidt, I | 424/478 |
| 4,875,247 | 10/1989 | Berg | 15/104.94 |
| 4,925,670 | 5/1990 | Schmidt, II | 424/443 |

FOREIGN PATENT DOCUMENTS

| | | |
|---|---|---|
| 0219762 | 4/1987 | European Pat. Off. . |
| 0259749 | 3/1988 | European Pat. Off. . |
| 1476057 | 6/1977 | United Kingdom . |
| 2163348 | 2/1986 | United Kingdom . |
| 2186190 | 8/1987 | United Kingdom . |

*Primary Examiner*—Shep K. Rose
*Attorney, Agent, or Firm*—Cushman, Darby & Cushman

[57] ABSTRACT

A mouth and tooth care preparation consists of tensides, polishing agents, aromatizing agents as well as additional usual additives which are formulated in a binding agent or a mixture of binding agents consisting of water-soluble or water-swellable, physiologically acceptable film-forming agents. The mixture is formulated into a film which is pre-segmented into dosage units.

6 Claims, No Drawings

ORAL AND DENTAL HYGIENE PREPARATION

This is a continuation of application Ser. No. 07/689,862, filed on Aug. 13, 1991, now abandoned which was abandoned upon the filing hereof of the present FWC application.

Tooth care preparations have been prepared for many years in the form of pastes, the so-called toothpastes. Herein the starting material is essentially a precipitated calcium carbonate which has been formulated with water, glycerol, surface-active substances and thickening agents to obtain a paste and is filled into tubes or dispensers. The toothpaste has conquered the market while other tooth care preparations like drops, tooth soaps and powders or pellets scarcely play a role any more. The preparations are proposed to remove the bacterial plaque, to serve for caries prophylaxis and for the careful cleaning of the teeth substantially supported by brushing, and to thoroughly clean the mouth cavity and refresh the same in a pleasant manner.

During recent years the picture of the toothpastes has not substantially changed although the formulas have been modified in various aspects. The use of a rather coarse form of calcium carbonate for mechanically cleaning the teeth has more and more been replaced by modern, finer polishing agents on the basis of aluminum oxide or silicium dioxide (silica gel). Next to tensides structure-forming components and sophisticated taste correcting agents are used. Often active agents like particularly various fluoro derivatives or mineral salts are added. The volume could sometimes be reduced; certainly the introduction and general use of electric toothbrushes has had a strong influence in this regard.

The handling of toothpastes is, however, accompanied by a number of disadvantages. Because the dosing from simple tubes is difficult, dispensers have recently been developed which always deliver a predetermined amount of toothpaste. These dispensers are, however, relatively big and therefore scarcely suitable for use when travelling. Tubes are pressure-sensitive and therefore also not ideal when travelling. In dispensers as well as in tubes toothpaste can dry out during longer interruptions of use, so that the used receptacles have to be discarded. In addition it is not possible to completely empty tubes as well as dispensers. After use the receptacles made from metal or plastic are retained and cause pollution.

In contrast it is the object of the present invention to provide a new administration and dosage form for mouth and tooth care preparations which does not develop the aforementioned disadvantages. In particular it is the object to make possible and secure exact dosage for the single toothcleaning procedure and to provide the possibility to completely use the preparation without remains staying in the package.

The mouth and tooth care preparation of the invention on the basis of tensides, polishing agents, aromatizing substances as well as additional usual additives is characterized in that the active agents and additives are formulated in a binding agent or a mixture of binding agents which consists of water-soluble or water-swellable, physiologically acceptable film forming substances and that this mixture is formulated into a film whereby the so formed film is pre-segmented in dosage units.

The mouth and tooth care preparations may comprise such components which are normally used for the preparation of toothpastes, with natural starting materials being particularly preferred. In addition it is important for all components to be completely non-toxic and physiologically acceptable which, of course, also applies to the film forming substances to be used. The following components are to be mentioned as the essential components of tooth care preparations:

- abrasives like calcium carbonate, calcium and sodium phosphate, aluminum oxide or silicium dioxide, particularly silica gels
- tensides (foaming agents) like sodiumlaurylsulfate, sodiumlaurylsulfoacetate, sarcoside, monoglycerylsulfate and others
- aromatizing agents like peppermint oil, spearmint oil, aniseed oil, cinnamon oil, oil of cloves, menthol and the like
- sweetening agents like saccharin, cyclamate, aspartame and the like.

The liquid components usually present in toothpastes like glycerol, propylene glykol or sorbite syrup do not have to be added to the preparations according to the invention in film-form, since the plasticity necessary for tubes or dispensers does not play a role in this regard. Additional usual additives like fluoro compounds, agents against the forming of tartar, antibacterial agents and the like, as normally used in mouth and tooth care preparations can also be used according to the invention.

As water-soluble or water-swellable film-forming agents starch, gelatines, glycerols and/or sorbite are particularly suitable as well as natural and synthetic resins and gums. The following basic formulation has proved suitable:

| | |
|---|---|
| gelatine | 8–10 g |
| starch | 3–8 g |
| glycerol | 1–2 g |
| water | 30–50 g. |

In this basic material the components of the mouth and tooth care preparations are dissolved or dispersed to obtain a uniform distribution of the substances. The mixture so obtained can according to the invention be formulated in various manner into mouth and tooth care preparation in the form of a film:

a) It is in the first place possible to formulate the mass directly into a foil which generally will have a thickness of between 0.1 and 3 mm. Through predetermined fraction points this foil can be pre-segmented into dosage units by punching or perforation with the strip broadness and length preferably corresponding to about the size of the toothbrush, i.e. of the surface formed by the free bristle ends of the bristle block or the surface of the longitudinal cross-cut of the bristle block in the bristle level.

b) Alternatively the mass can be applied onto a carrier film, the composition of which corresponds to the binding agent of the mass, as disclosed in detail in EP-OS 219 762. The films obtained in this manner can also be pre-segmented as indicated above.

c) In addition it is possible to apply the mass onto a release film or release paper as known from DE-PS 36 30 603. In this case the coating is pre-segmented in separate segments of the size as indicated above which prior to use can be peeled off the carrier film in a manner similar to adhesive stickers.

In all cases an administration and dosage form is obtained, the application of which is particularly convenient since the amount to be used is uniformly predetermined in each case. A dosage is separated or peeled off in a form of a film segment and is placed onto the moistened toothbrush or between the bristles where it adheres and swells through moisture contact. Through the insertion into the mouth cavity and in connection with the saliva and the intensive movement of the toothbrush the strip is pre-dissolved and dissolved so that the components can develop their full activity. After use and subsequent mouth washing with water no remains are retained in the mouth.

Optionally the foils can be printed, stamped or punched in various manners, with the possibility to apply designs particularly for children. The opening and closing of tube closures is not necessary, no toothpaste is spoiled and the administration form of the invention is particularly suitable for travelling, since it is light of weight, no leaking has to be taken into account and it occupies extremely little space. Packaging is possible in non-polluting cardboard cases without the use of metals or plastics.

The preparations of the invention are suitable not only for tooth care in the mouth but also, given a suitable composition, for cleaning and care of artificial teeth and dentures. For the last mentioned purpose a multiple coating is particularly advantageous, which comprises the cleaning, disinfecting and acidic components in one layer, while, optionally separated by an also water-soluble barrier layer, the second layer comprises the $CO_2$ or $O_2$ releasing substances.

EXAMPLE

A tooth care preparation according to the invention has the following composition:

| | |
|---|---|
| amylogum | 57.0 g |
| honey | 25.0 g |
| citric acid | 2.0 g |
| titanium dioxide | 1.0 g |
| aromatizing agents | 1.0 g |
| silicium dioxide | 3.0 g |
| Ca-hydrog.-phos. | 10.0 g |
| Na-laurylsulfate | 1.0 g |

A slurry is formed using the necessary amount of water which is formulated into a film having a thickness of about 0.5 mm. The film is segmented into segments of 8×35 mm by perforation.

Optionally the mass can be applied onto release paper as carrier and can be pre-segmented in segments of the size as indicated above by punching.

I claim:
1. A mouth and tooth care preparation comprising foaming agents, polishing agents, aromatizing agents and other additives wherein said foaming agents, polishing agents, and aromatizing agents and said additives are mixed with at least one binding agent or a mixture thereof, said binding agent including a water-soluble, physiologically acceptable film forming substance;
   said mixture is in the form of a pre-segmented film or foil dentrifice, oral hygiene mouth and toothcare strip comprising segmented dosage units, said dose units being conformed and sized to be fitted on, or placed between, the moistened bristles or on the moistened free bristled end on the moistened bristle block of a toothbrush;
   said dosage unit strip being adhered to a carrier film, release film or release paper and can be peeled off said carrier film, release film or release paper and thereby utilized independent of other dosage units present on said carrier film, release film, or release paper; and
   each of said dose units, subsequent to fitting, adheres, swells, and dissolves upon moisture contact such that no remains are retained in the mouth after usage and subsequent mouthwashing.
2. Mouth and tooth care preparation according to claim 1 wherein said film forming substance is selected from the group consisting of a starch, a gelatin, or mixtures thereof.
3. Mouth and tooth care preparation according to claim 1, characterized in that it contains amylogum as film forming agent.
4. Mouth and tooth care preparation according to claim 1, characterized in that it consist of a carrier film comprising the binding agent or the mixture of binding agents, onto which a layer has been applied, which contains the components of the care preparation together with binding agent or the mixture of binding agents, the binding agent or the mixture of binding agents in the carrier film and in the coating having substantially the same qualitative composition.
5. Mouth and tooth care preparation according to claim 2 wherein said film forming substance further comprises a plasticizer selected from the group consisting of glycerol and sorbitol.
6. The dosage unit strip of claim 1 wherein said film or foil comprises 8–10 parts per weight of gelatin, 4–8 parts per weight of starch, and 1–2 parts per weight of glycerol.

* * * * *